United States Patent
Shimoda et al.

Patent Number: 5,624,686
Date of Patent: Apr. 29, 1997

[54] FEED ADDITIVES FOR FATTENING PIGS, FEED FOR FATTENING PIGS, AND METHOD OF FATTENING PIGS

[75] Inventors: Minoru Shimoda, Tokyo; Ei-ichi Kokue, Kokubunji, both of Japan

[73] Assignee: Ajinomoto Co., Inc., Tokyo, Japan

[21] Appl. No.: 401,803

[22] Filed: Mar. 10, 1995

[30] Foreign Application Priority Data

Sep. 9, 1994 [JP] Japan .................................. 6-215857

[51] Int. Cl.$^6$ .................................................. A61K 9/14
[52] U.S. Cl. ........................ 424/489; 424/488; 424/490; 424/442
[58] Field of Search ............................... 424/489, 488, 424/490, 442

[56] References Cited

U.S. PATENT DOCUMENTS

| | | | |
|---|---|---|---|
| 3,912,811 | 10/1975 | Arai et al. | 424/118 |
| 3,949,070 | 4/1976 | Arai et al. | 424/118 |
| 4,666,891 | 5/1987 | Ginsberg et al. | 514/45 |

*Primary Examiner*—Thurman K. Page
*Assistant Examiner*—William E. Benston, Jr.
*Attorney, Agent, or Firm*—Oblon, Spivak, McClelland, Maier & Neustadt, P.C.

[57] ABSTRACT

Feeding fattening pigs a feed additive which contains as an active ingredient active folic acid (in the form of leucovorin, $H_2$-folic acid, a liver powder, disrupted cells of a microorganism or a cell extract of a microorganism), or a feed for fattening pigs and lactating sows which contains such an additive, either directly orally or via breast milk, is effective for increasing the amount of a reduced form of folic acid in the plasma of the fattening pigs and improving the efficiency of fattening.

7 Claims, 1 Drawing Sheet

FEED ADDITIVES FOR FATTENING PIGS, FEED FOR FATTENING PIGS, AND METHOD OF FATTENING PIGS

BACKGROUND OF THE INVENTION

1. Field of the Invention

The present invention relates to feed additives for fattening pigs and lactating sows which contain a reduced form of folic acid as an active ingredient, increase the amount of a reduced form of folic acid in the plasma of fattening pigs, and improve the fattening efficiency of fattening pigs; and to a feed for fattening pigs and lactating sows which contains such a feed additive. The present method also relates to a method of fattening pigs by feeding pigs such a feed additive or feed.

2. Discussion of the Background

Folic acid is a coenzyme participating in the synthesis of amino acids, such as methionine, serine, and glutamic acid, and purine bases of the nucleic acids which constitute DNA. It has been confirmed by epidemiological surveys on pregnant women and tests on pregnant guinea pigs that the demand for folic acid increases and its concentration in blood plasma decreases in mother's bodies during pregnancy (Pritchard J. A. et al., *Am. J. Obst. Gynecol.*, Vol. 104, p. 388 (1969) and Habibzadeh H. C. et al., *Br. J. Nutr.*, Vol. 55, p.23 (1986)).

It has also been confirmed with regard to domestic pigs, that the amount of reduced forms of folio acid in the blood plasma of sows decreases during pregnancy (Natsuhori et al., Final Program and Abstracts Book of the 10th International Symposium: "Chemistry and Biology of Pteridines and Folates," p.196 (1993)). It has also been proven that breeding efficiency can be improved by administering folic acid (an oxidized form) to pregnant pigs by means of intramuscular injection (Matte J. J. et al., *J. Anim. Sci.*, Vol. 67 p. 426 (1989) and Friendship R. M. et al., *Can. Vet. J.*, Vol. 32, p.564 (1991)), which shows the importance of administering folic acids to pregnant pigs (sows).

Meanwhile, there has been only little study regarding the influence which folic acid has on fattening pigs for meat in terms of fattening efficiency. In one study conducted by J. J. Matte, et al., the level of folic acid (in an oxidized form) in the plasma was found to increase by intramuscularly injecting folic acid to fattening pigs every week without a change in the weight increase, and the feed efficiency tended to improve (*Reprod. Nutr. Dev.*, vol. 30, pp. 103–114 (1990)). In the other study conducted by J. J. Matte, et al., it was reported that when folic acid (in an oxidized form) is intramuscularly injected in lactating sows, the level of folic acid in breast milk and in the plasma of suckling baby pigs increases but no influence is found in terms of weight increase (*J. Anim, Sci.*, vol. 67, pp. 426–431 (1989)).

In general, folic acid is chemically synthesized. Chemically synthesized folic acid is of an oxidized form, and an oxidized form of folic acid per se does not function as a coenzyme. Usually, after being absorbed into the body, it is transformed by dihydrofolic acid dehydrogenase into 7,8-dihydrofolic acid ($H_2$ folic acid), which is then enzymatically reduced to reduced forms of folic acid such as tetrahydrofolic acid (THF) or 5-methyltetrahydrofolic acid (5 MF) which act as coenzymes. Therefore, the effect of the administration of folic acids can be determined by measuring the amount of THF or 5 MF in the blood plasma. However, it is not possible to determine the amount of the reduced forms of folic acid alone in a selective manner by the known determination method since it is based on the radioligand technique, and hence it is not possible to obtain an accurate value of the amount of the reduced forms of folic acid contained in the blood plasma. In the present specification, the reduced forms of folic acid may also be referred to as "active-type folic acids" since they have physiological activities, and the oxidized forms of folic acid may also be referred to as "inactive-type folic acids" since they have no physiological activities.

For the purpose of analyzing the effects of administering folic acids to pigs, the HPLC-ECD method has been developed recently for determining the content of the active-type folic acids in the blood plasma by high performance liquid chromatography using an electrochemical detector, and, by using this method, investigations have been made on the extent of appearance of THF and 5 MF in blood plasma at the time when folic acid (an oxidized form) is administered to pigs by intravenous injection, intramuscular injection or oral administration. To be more specific, 4 grown-up pigs having a body weight of around 25 kg were distributed according to the Latin square method to 4 factors: intravenous injection (1 mg/kg of body weight), intramuscular injection (1 mg/kg of body weight), small dosage oral administration (1 mg/kg of body weight) and large dosage oral administration (50 mg/kg of body weight), of folic acid (in an oxidized form), and tests were performed. As a result, the concentration of THF and 5 MF in the blood plasma increased in the cases of intravenous injection, intramuscular injection and large dosage oral administration. Accordingly, it is considered that the administered folic acid (an oxidized form) was adsorbed and converted to active-type folic acids in the liver, etc. On the other hand, THF and 5 MF did not appear in the blood plasma in the case of small dosage oral administration. With regard to the above, see Eiichi Kokue et al., "Abstract Book of the 113th Convention of Japan Veterinary Society." p. 112 (1992). In rats, it has been known that the concentration of reduced forms of folic acid increase rapidly even when an oxidized form of folic acid is administered in a small dosage (Tsunematu K. et al., *Cong. Anom.*, Vol. 30, p. 113 (1990)).

From the above, it is considered that pigs possess a capability of converting inactive-type folic acids to active-type folic acids, but their capability of absorbing inactive-type folic acids from the digestive tract is far less than rats. It has also been found that an extremely large quantity of inactive-type folic acids must be administered to pigs in order to increase the amount of active-type folic acids in the blood plasma by oral administration of inactive-type folic acids.

Thus, there remains a need for feed additives for fattening pigs which increase the amount of reduced forms of folic acid in the plasma and which improve the efficiency of fattening pigs, feeds for fattening pigs which contain such an additive, and a method of fattening pigs by feeding pigs or lactating sows such a feed additive or feed.

SUMMARY OF THE INVENTION

Accordingly, it is one object of the present invention to provide novel feed additives for fattening pigs.

It is another object of the present invention to provide novel feed additives for fattening pigs which increase the amount of a reduced form of folic acid in the plasma of fattening pigs.

It is another object of the present invention to provide novel feed additives for fattening pigs which improve the fattening efficiency of fattening pigs.

It is another object of the present invention to provide novel feeds for fattening pigs which contain such a feed additive for fattening pigs.

It is another object of the present invention to provide a novel method for fattening pigs by feeding a fattening pig or a lactating sow such a feed additive or feed.

These and other objects, which will become apparent during the following detailed description, have been achieved by the inventors' discovery that orally administering either directly or via breast milk a feed additive which contains a reduced form of folic acid or a feed containing such a feed additive is effective for increasing the concentration of a reduced form of folic acid in the plasma of fattening pigs and for improving the fattening efficiency. Thus, the present inventors have found that the concentration of a reduced form of folic acid in the plasma of fattening pigs can be increased by administering a reduced form of folic acid orally as such or by adding it to the feed or by administering it via breast milk.

That is, the present invention relates to an improvement in the fattening efficiency with regard to fattening pigs by administering a reduced form of folic acid orally.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
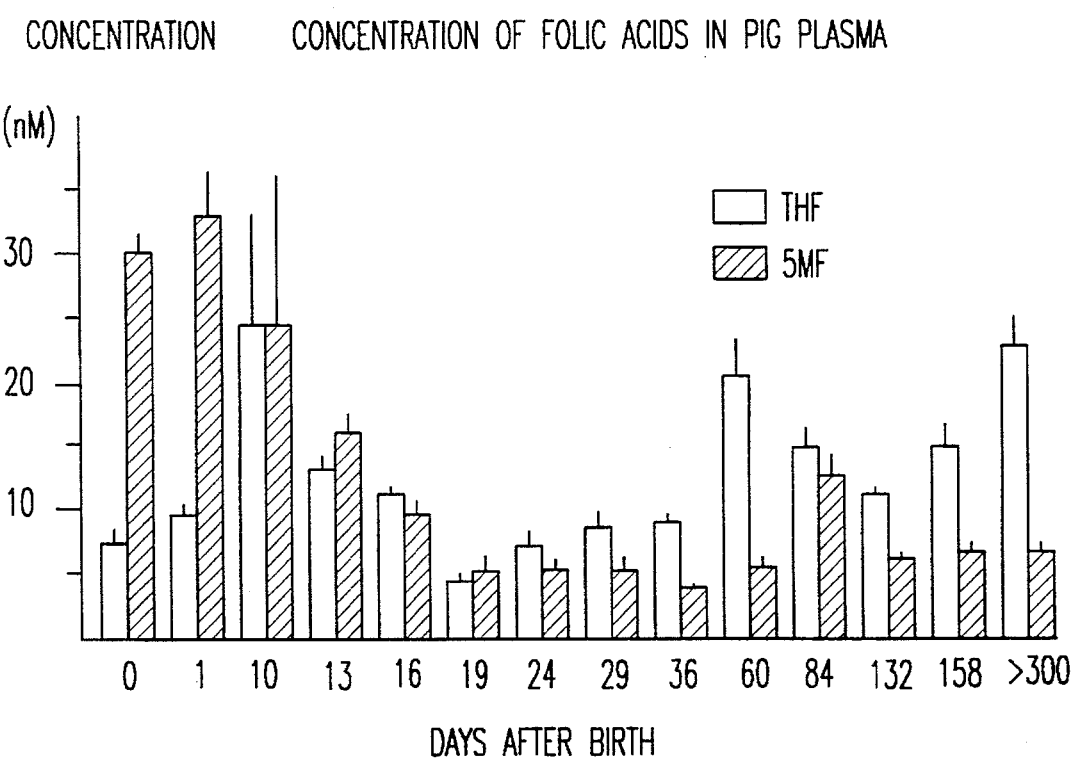
FIG. 1 is a bar graph showing the concentration of THF and 5 MF in pig plasma as a function of days after birth.

The present inventors have studied the variation in the concentration of the active folic acid in plasma of mature or pregnant pigs, and have then arrived at the following finding. Fattening pigs before or after weaning were found to have significantly low concentrations of active folic acid compared to pregnant breeding pigs. It was therefore shown that the fattening can be improved by supplying folic acid during this period (refer to the Experiment 1 given hereinafter), On the basis of the above-mentioned finding, the present invention firstly provides a feed additive for fattening pigs and lactating sows which contains a reduced form of folic acid as an active ingredient to improve the fattening efficiency.

In this invention, improving the fattening efficiency in the fattening pigs means that when the feed additive of the present invention is directly administered orally to fattening pigs directly or via breast milk or when the fattening pigs are fed with the feed of this invention, the weight of the fattening pigs can be rapidly increased and the feeding period before sending them to the market can be therefore shortened or the fattening efficiency can be improved, as compared to the case where the fattening pigs are fed in exactly the same way except for the administration of active folic acid.

In the present invention, the term "a reduced form of folic acid" includes not only a reduced form of folic acid in its narrow sense (pteroyl(mono)glutamic acid), but also a reduced form of other various folic acids (folic acids in its wider sense). It should be noted that the definition of a reduced form of folic acid includes such reduced forms of folic acid which show the physiological functions similar to the reduced form of folic acid in its narrow sense.

Accordingly, in the present invention, reduced forms of folic acid include folic acids whose pteridine ring is reduced, such as 7,8-dihydrofolic acid ($H_2$ folic acid); $H_4$folic acids, such as 5,6,7,8-tetrahydrofolic acid ($H_4$ folic acid), 5-formyl-$H_4$-folic acid, e.g. leucovorin [L-(−)-5-formyl5,6, 7,8-tetrahydrofolic acid], 5,10-methylen-$H_4$-folic acid, 5-methyl-$H_4$-folic acid, 10-formyl-$H_4$-folic acid, 5-methyl-$H_4$-folic acid, 5-formimino-$H_4$-folic acid, etc.; and derivatives, such as poly-gamma-glutamic acid derivatives of each $H_4$ folic acid (known as storage-forms of folic acid in liver). It is a matter of course that in the present invention the reduced form of folic acid can also be in the form of liver powders and digested cells (disrupted cells) of a microorganism containing it.

The liver is an organ in which various vitamins are metabolized, and the content of reduced forms of folic acid in the liver is known to be relatively high. However, there is no example in which a liver powder formed by freeze-drying the liver of a swine, a bovine or the like and pulverizing it is orally administered to fattening pigs to improve the fattening efficiency. It is a new finding made by the present inventors that a feed is mixed with a liver powder to increase the concentration of THF or 5 MF in the plasma of fattening pigs.

The disrupted cells and the cell extract of a microorganism are described hereinafter. It is already well known that a yeast extract functions as a source of various vitamins. The yeast extract is a material obtained by self-digesting the yeast and disrupting the cell wall. Various vitamins are leaked outside the cells, and thus can be easily absorbed.

A yeast such as Torula yeast is used in feed as a source of vitamins. However, since cells without disruption of the cell wall or extraction are generally used, the vitamins contained in the cells are poorly absorbed.

In view of the above, the present inventors have conducted intensive investigations and have found that the amount of THF and 5 MF in the blood plasma of pigs can be increased by orally administering products prepared by subjecting cells of a microorganism to a mechanically disruption treatment, to an enzymaticlly digestion treatment, or to autolysis so as to make the reduced forms of folic acid in the cells into a readily absorbable condition (disrupted cells of a microorganism), or products prepared by extracting cells of a microorganism. Accordingly, the fattening efficiency can be improved by administering the product to fattening pigs.

The microorganism used as a raw material for preparing the disrupted cells or the cell extract of the microorganism in this invention may be any microorganism if the content of a reduced form of folic acid in the disrupted cells (mechanically disrupted or enzymatically digested products) or the cell extract is high. Specific examples of the microorganism include bacteria such as *Corynebacterium glutamicum* (former name *Brevibacterium lactofermentum*) ATCC 13869, *Corynebacterium ammoniagenes* (former name: *Brevibacterium ammoniagenes*) ATCC 6871, *Corynebacterium glutamicum* (former name: *Brevibacterium flavum*) ATCC 13826, *Corynebacterium glutamicum* ATCC 13032 and ATCC 13060, *Bacillus subtilis* ATCC 13952, IFO 3009 and IFO 13169, and *Lactococcus lactis* subsp. cremoris ATCC 19257; yeasts such as *Saccharomyces cerevisiae* IFO 2044 and IFO 2375, and *Candida utilis* (former name: *Torulopsis utilis*) ATCC 9226; and molds such as *Aspergillus niger* IFO 4414.

These microorganisms can be usually cultivated in any culture medium that contains a nutrient which the microorganisms can utilize. For example, an ordinary culture medium can be used which appropriately contains a carbon source, for example, carbohydrate such as glucose, sucrose, etc., an alcohol such as ethanol, glycerol, etc., an organic acid such as acetic acid, propionic acid, etc., soybean oil, or a mixture thereof; a nitrogen-containing inorganic or organic nutrient such as a yeast extract, peptone, meat extract, corn steep liquor, ammonium sulfate or ammonia, etc.; an inorganic nutrient such as a phosphate salt, magnesium, iron, manganese or potassium, etc.; and vitamin such as biotin or thiamine, etc.

In the cultivation, the typical conditions which are conventionally employed in the cultivation of these microorganisms may be applied. For example, the microorganisms may be aerobically cultivated at 20° to 40° C. for a period of 12 hours to 5 days in a nutrient culture medium at a pH range of 4.0 to 9.5.

The amount of reduced forms of folic acid produced in the cells of a microorganism obtained by the culturing may be increased by adding p-aminobenzoic acid, an oxidized form of folic acid, and/or a nucleic acid in the culture medium. The nucleic acid used preferably contains guanosine, inosine, xanthine, 5'-guanilic acid, 5'-inosinic acid, 5'0-xanthylic acid, guanosine-5'-diphosphate, and guanosine-5'-triphosphate. These additives can be added to the medium in an amount where the amount of reduced forms of folic acid produced in the cells can be increased, in comparison with cases where the additives are not added; for example, in an amount of 1 mg/liter to 1 g/liter, preferably 10 to 100 mg/liter. If the amount added is too small, no effects will be attained, whereas if it is too much, the growth of the microorganism may be inhibited.

The cells thus obtained by cultivating the microorganism as mentioned above are first separated from the culture solution by an appropriate method, and then subjected to a disruption or extraction treatment. But the culture can be subjected to the disruption or extraction treatment directly or after concentration, when the ingredients of the culture medium may be orally administered to the pigs and if they do not affect the performance of the disruption treatment. Furthermore, the cells to be subjected to the disruption or extraction treatment can be live cells or killed cells.

There is no particular restriction on the method of disruption of the cells. For example, the disruption can be performed by a hitherto known mechanical method, as well as by a method utilizing enzymes. Mechanical methods per se can be carried out in accordance with prior ones. For example, the cells of a microorganism can be disrupted with glass beads by using "Beads Beater"(manufactured by Biospec Co.), or the disruption of the cells can be performed with pressure, or can be carried out by using an ultrasonic disrupter. Also, in the case where the cells of a microorganism are disrupted by an enzyme, the method per se can be carried out in accordance with a prior method. For example, after the cultured cells have been subjected to a heat sterilization treatment as they are, a cell wall digesting enzyme may be added thereto, to decompose the cell walls of the microorganism. For this decomposition, any enzyme can be used, provided that it is capable of digesting and disrupting the cell walls. Well-known enzymes such as lysozyme, protease, zymolyase, and the like, are typical examples of the enzymes having such a capability. The enzymatic treatment can be carried out in accordance with known conditions. The extraction method is not particularly limited either. For example, the extraction can be conducted with hot water at a temperature of from 90° to 120° C.

The thus-prepared disrupted cells or extract is orally administered to fattening pigs as is or in a appropriate concentrated or dried form, or in a form of a mixture with an appropriate additive. Since folic acids are not generally abundant in the cell wall, remaining fragments of the cell wall may be removed from the disrupted cells. The form in which folic acid is orally administered to the fattening pigs also includes feeding the fattening pigs with a feed to which has been added the disrupted cells or the cell extract.

The reduced forms of folic acid in various forms may be used either individually or in combination.

Taking into consideration the convenience of use, the feed additive for fattening pigs and lactating sows according to the present invention can be distributed in an appropriate dosage form, including concentrates, dried powders, granules, etc., with or without addition of appropriate carriers or the like.

This invention also provides a feed for fattening pigs and lactating sows which contains the feed additive for fattening pigs of this invention. Thus, the present feed comprises: (a) a feed additive which comprises a reduced form of folic acid; and (b) a base feed.

No particular difficulty is involved in producing such a feed for fattening pigs and lactating sows. The feed can be produced according to a known process for producing a mixed feed except that the feed additive for fattening pigs in this invention is mixed with the base feed.

When mixing the feed additive for fattening pigs of the present invention, special care should be taken with regard to the mixing amount. The amount of the feed additive for fattening pigs in the feeds of the present invention is an amount at which the effect provided by the additive is exhibited, for example, an amount which is such that the daily intake of the feed additive calculated in terms of a reduced form of folic acid is from 0.1 to 100 µg/kg·weight of the fattening pig, preferably 1 to 50 µg/kg·weight of the fattening pig. When the amount is too small, the effect is not exhibited. However, an amount larger than the above range does not increase the effect and is useless.

Base feeds suitabled for preparing the feeds of the present invention are described in Kirk-Othmer, *Encyclopedia of Chemical Technology*, 4th Ed., vol. 10, pp. 288–300, Wiley, N.Y., 1993, which is incorporated herein by reference. Preferably, the base feed will comprise one or more of the following ingredients corn, sorghum, barley, wheat, soybean, peanut, canola, fish meal, milk products, fats and oils, vitamins, and minerals.

Thirdly, the present invention provides a method for feeding fattening pigs which comprises orally administering the feed additive of the present invention to the fattening pigs either directly or via breast milk, or by feeding the fattening pigs with the feed for fattening pigs of the present invention.

No special difficulty is found with this feeding method, and the feeding can be conducted by means of a conventional method except that the daily intake of a reduced form of folic acid is to be from 0.1 to 100 µg/kg·weight of the fattened pig, preferably form 1 to 50 µg/kg·weight of the fattening pig.

The period of direct oral administration and the feeding period in the feeding method of this invention is described below. Since a reduced form of folic acid is administered to improve the fattening efficiency of fattening pigs, oral intake of a reduced form of folic acid may be started immediately after birth and be continued, for example, until approximately one month after birth which corresponds to the weaning period and further until some period up to approximately three months after birth.

Active folic acid can be administered to fattening pigs via the breast milk of sows during the suckling period. Specifically, the feed additive of lactating sows in this invention is orally administered to the lactating sows, or the sows are fed with the feed for lactating sows of the present invention during the lactation period. In this way, active folic acid absorbed in the sows is transferred to the breast milk and then administered to the suckling fattening pigs via the breast milk.

Other features of the invention will become apparent in the course of the following descriptions of exemplary embodiments which are given for illustration of the invention and are not intended to be limiting thereof.

EXAMPLES

Experiment 1

(Variations in the concentration of active folic acid in the plasma according to the growth of pigs).

(a) MethOd:

A blood sample was taken from 109 fattening pigs which are either newborn or up to 5 months old, and the concentrations of THF and 5 MF in the plasma were measured by a reverse-phase HPLC method.

The measurement method is described in detail below. That is, 0.2 ml of 0.5M perchloric acid was added to 0.2 ml of the blood samples, and the solution was subjected to centrifugal separation of 5,000 g×2 minutes to remove protein. One hundred microliters of the obtained supernatant solution were subjected to high-performance liquid chromatography. Regarding the conditions for analysis, a "Phenyl-bonded phase column of 4.6 mm$\phi$×150 mm" (manufactured by Irica Co.) was used, a mixed solution of a 20 mM potassium acetate buffer (pH 3.6) and acetonitrile at a ratio of 97.5:2.5 (v/v) was used as the mobile phase, and the flow rate was 0.8 ml/min. The detection was conducted with "Electrochemical Detector E-502 Model"(manufactured by Irica Co.), and the voltage applied was −300 mV.

(b) Results:

The results are shown in FIG. 1. From FIG. 1, it follows that the newborn fattening pigs exhibited quite a high 5 MF concentration (32±8 nM) and a THF concentration (8.3±2.8 nM) which was ⅓ or less than the 5 MF concentration. However, as the fattening pigs grew, the 5 MF concentration decreased. After the fattening pigs were weaned, the 5 MF concentration was approximately equal to the THF concentration, and when the fattening pigs became 1 month old, the concentrations were inverted (THF concentration 8±3.7, 5MF concentration 4.6±3.1 nM). Thereafter, the THF concentration gradually increased until the fattening pigs became 3 months old, and the 5 MF concentration remained almost constant. When the fattening pigs became 5 months old, the THF concentration was 14±5.4 and the 5 MF concentration was 5.5±2.4 nM.

This experiment shows that the concentration of a reduced form of folic acid in the blood decreases considerably before or after the weaning, and from this it can be understood that the oral administration of active folic acid is effective for improving the fattening efficiency of fattening pigs.

EXAMPLE 1

(Production of disrupted cells of a microorganism).
(a) Cultivation of a microorganism:

Into 500 ml flasks was poured 50 ml each of a culture medium having the composition shown in Table 1 set forth below. After sterilization by heating, one platinum loopful of cells of each of the microorganisms shown in Table 2 were inoculated in the medium and cultured with shaking at 30° C. for 24 to 78 hours. The bacteria used were previously cultured on a bouillon agar medium at 30° C. for 24 hours, and the yeasts and molds used were previously cultured on a malt extract agar medium at 30° C. for 48 to 72 hours. After the culturing, cells were collected by centrifugation.

TABLE 1

| Components | Concentration |
| --- | --- |
| Glucose | 2.0 g/dl |
| Yeast Extract | 1.0 g/dl |
| Polypeptone | 1.0 g/dl |
| $(NH_4)_2SO_4$ | 0.5 g/dl |
| $K_2HPO_4$ | 0.3 g/dl |
| $KH_2PO_4$ | 0.1 g/dl |
| $MgSO_4.7H_2O$ | 0.05 g/dl |
| $FeSO_4.7H_2O$ | 0.001 g/dl |
| $MnSO_4.4H_2O$ | 0.001 g/dl |
| pH 7.0 | |

TABLE 2

| | Microorganisms | Contents of Folic acids (mg/100 g) | |
| --- | --- | --- | --- |
| | | Before Disruption | After Disruption |
| Bacteria | Corynebacterium glutamicum ATCC 13869 | 2.0 | 12.0 |
| | Corynebacterium ammoniagenes ATCC 6871 | 1.3 | 8.9 |
| | Brevibacterium flavum ATCC 13826 | 2.8 | 14.2 |
| | Corynebacterium glutamicum ATCC 13032 | 1.5 | 10.8 |
| | Corynebacterium glutamicum ATCC 13060 | 3.5 | 9.0 |
| | Corynebacterium glutamicum ATCC 13952 | 1.6 | 5.6 |
| | Bacillus subtilis IFO 3009 | 0.9 | 4.7 |
| | Bacillus subtilis IFO 13169 | 2.8 | 8.3 |
| | Lactococcus lactis subsp. cremoris ATCC 19257 | 2.1 | 7.8 |
| Yeasts | Saccharomyces cerevisiae IFO 2044 | 0.3 | 3.8 |
| | Saccharomyces cerevisiae IFO 2375 | 0.7 | 4.0 |
| | Candida utilis ATCC 9226 | 0.1 | 2.9 |
| Molds | Aspergillus oryzae IFO 30104 | 1.1 | 5.8 |
| | Aspergillus niger IFO 4414 | 1.6 | 7.6 |

(b) PreparatiOn of disrupted cells of microorganisms:

The microorganisms so collected were suspended into physiological saline of a volume equal to the culture medium and then subjected to a heat treatment (sterilization) at 100° C. for 10 minutes, and the cells were again collected by centrifugation. The cells were suspended in a 25 mM phosphate buffer (pH 7.0) at a concentration of 10% by wet weight.

With regard to bacteria, 0.1% by weight of egg-white lysozyme (produced by Sigma Co.) and 0.2% by weight of papain (produced by Amano Pharmaceutical Co.) were added to the thus prepared suspensions of the cells, and the cell walls were digested and disrupted by maintaining the mixture at 37° C. for 12 hours, to obtain a disrupted cell liquid. With regard to yeasts, 0.2% by weight of "Zymolyase 20T," a yeast cell wall digesting enzyme (produced by Seikagaku Kogyo K.K.), was added, and the cell walls were digested and disrupted by also maintaining the mixture at 37° C. for 12 hours, to obtain a disrupted cell liquid. With regard to molds, the suspensions of cells were added with the same quantity (by volume) of glass beads of 0.75 mmφ, and the mixture was subjected 5 times to the cell disruption treatment of 1 minute by using "Beads Beater"(produced by Biospec Co.) and then to decantation, to obtain a supernatant by removing glass beads.

Each of the thus-obtained disrupted cell liquids and supernatant fluids of bacteria, yeasts and molds was dried by freeze-drying to obtain powders (one of the distribution form of the feed additive for sows according to the present invention).

(c) Quantitative analysis of the content of folic acid:

The amount of folic acids contained per 100 g of the thus-obtained dried powders was determined by means of bioassay using *Enterococcus hirae* ATCC 8043. Results obtained are also shown in Table 2. In this bioassay, both the active-type folic acids (reduced forms) and inactive-type folic acids (oxidized forms) are determined at the same time to give their total amount. However, the value so determined may be regarded to be mostly based on active-type since the folic acids contained in the dried powders are derived from microorganisms.

Example 2

(Production of mechanically disrupted cells of bacteria).

In a similar manner as in Example 1, *Corynebacterium glutamicum* ATCC 13869 and *Corynebacterium glutamicum* ATCC 13060 were cultured, and their cells were collected and suspended into 20 mm phosphate buffer (pH 7.0) at 10% by weight, to prepare cell suspensions.

The cell suspensions were admixed with the same quantity of glass beads of 0.1 mmφ, and the cells were completely disrupted by repeating 10 times disruption treatment of 1 minute by using "Beads Beater." Thereafter, the resulting products were subjected to centrifugal separation, to separate the cytoplasm fractions into the centrifugal supernatant and the cell wall fractions into the centrifugal residues.

Each of the fractions were dried by freeze-drying, and the amount of folic acids present in 100 g of dried products was determined by means of bioassay as in Example 1. Results obtained are shown in Table 3.

TABLE 3

| Bacteria | Contents of Folic Acids (mg/100 g) | |
|---|---|---|
| | Cytoplasm Fraction | Cell Wall Fraction |
| *Corynebacterium glutamicum* ATCC 13869 | 13.6 | 0.006 |
| *Corynebacterium glutamicum* ATCC 13060 | 11.2 | 0.008 |

It is understood from Table 3 that folic acids are present in the cytoplasm fractions.

EXAMPLE 3

(Cultivation with the addition of folic acid precursors).

In a similar manner as in Example 1, digested products (disrupted products) of cells were prepared by enzymatic treatment of the cells using *Corynebacterium glutamicum* ATCC 13869 or *Corynebacterium glutamicum* ATCC 13060.

The cells used above were obtained by culturing the above bacteria with the addition of 100 mg/liter of p-aminobenzoic acid, 10 mg/liter of folic acid (an oxidized form), or 100 mg/liter of guanosine to the medium.

The content of folic acids contained in 100 g of dried powders is as shown in Table 4.

TABLE 4

| | Content of Folic Acids (mg/100 g) | | | | | |
|---|---|---|---|---|---|---|
| | With p-Aminobenzoic Acid Added Disruption Treatment | | With Folic Acid Added Disruption treatment | | With Guanosine Added Disruption treatment | |
| Bacteria | before | after | before | after | before | after |
| *Corynebacterium glutamicum* ATCC 13869 | 4.2 | 23.0 | 3.4 | 21.9 | 3.0 | 18.5 |
| *Corynebacterium glutamicum* ATCC 13060 | 3.6 | 22.4 | 2.9 | 18.7 | 3.8 | 15.7 |

Example 4.

(Feeding test).

A test was conducted using 12 suckling baby pigs. To prevent anemia, a prescribed amount of an iron agent was intramuscularly injected in the piglets at the time the test was started.

The piglets were divided into two groups as uniformly as possible taking the weight and the sex into account. To one group, leucovorin was administered, and to the other, a physiological saline solution (as a control).

With respect to the leucovorin-administered group, a commercial leucovorin injection (3 mg/ml) was diluted 30 times with a physiological saline solution (100 μg/ml), and 1 ml of the diluted injection was orally administered to the piglets with a dropping pipette every day at 2:00 p.m. from Day 4 to Day 23.

The blood sample was collected at 11:00 a.m. on Days 4, 9, 18, and 25, and the value of folic acid in the plasma was measured according to the method described in Experiment 1. The results are shown in Table 5.

TABLE 5

| Piglets | THF (nM) | | | | 5 MF (nM) | | | | Total (nM) | | | |
| --- | --- | --- | --- | --- | --- | --- | --- | --- | --- | --- | --- | --- |
| | Day 4 | Day 9 | Day 18 | Day 25 | Day 4 | Day 9 | Day 18 | Day 25 | Day 4 | Day 9 | Day 18 | Day 25 |
| (a) Influence of oral administration of leucovorin on newborn pigs upon concentration of active folic acid in plasma | | | | | | | | | | | | |
| 1 | 13.2 | 25.0 | 18.0 | 25.0 | 28.2 | 16.6 | 18.3 | 16.7 | 41.4 | 41.5 | 36.3 | 41.7 |
| 2 | 26.2 | 25.6 | 32.1 | 28.8 | 55.5 | 21.5 | 27.6 | 16.1 | 81.6 | 47.1 | 59.6 | 44.9 |
| 3 | 24.7 | 21.9 | 21.6 | 25.7 | 40.7 | 12.2 | 12.2 | 9.3 | 65.4 | 34.1 | 33.8 | 35.1 |
| 4 | 26.8 | 28.1 | 24.2 | 27.6 | 50.7 | 20.2 | 11.9 | 11.3 | 77.6 | 48.3 | 36.1 | 38.9 |
| 5 | 17.2 | 14.8 | 19.0 | 24.0 | 19.8 | 11.3 | 8.9 | 6.0 | 36.9 | 26.0 | 27.9 | 30.0 |
| 6 | 8.8 | 21.6 | 13.4 | 19.6 | 30.7 | 16.6 | 7.4 | 4.5 | 39.5 | 38.2 | 30.8 | 34.1 |
| Average | 19.5 | 22.8 | 21.4 | 25.1 | 37.6 | 16.4 | 16.1 | 12.3 | 57.1 | 39.2 | 37.4 | 37.5 |
| (b) Concentration of active folic acid in plasma of control group | | | | | | | | | | | | |
| 7 | 10.3 | 17.3 | 14.7 | 27.6 | 38.7 | 16.0 | 11.4 | 15.9 | 49.0 | 33.3 | 26.1 | 43.5 |
| 8 | 19.0 | 16.8 | 12.5 | 23.4 | 36.6 | 16.4 | 10.6 | 19.8 | 55.5 | 33.2 | 23.0 | 43.2 |
| 9 | 20.2 | 19.4 | 16.5 | 18.9 | 22.9 | 15.0 | 8.8 | 18.8 | 43.2 | 34.5 | 25.3 | 39.7 |
| 10 | 21.1 | 25.0 | 15.2 | 14.0 | 33.0 | 20.6 | 9.3 | 16.0 | 54.1 | 45.6 | 24.5 | 30.0 |
| 11 | 24.4 | 18.1 | 15.6 | 18.7 | 29.4 | 14.7 | 6.1 | 13.1 | 53.8 | 32.8 | 21.8 | 31.8 |
| 12 | 15.6 | 14.1 | 21.3 | 16.7 | 37.6 | 9.9 | 9.7 | 9.6 | 53.3 | 24.0 | 31.0 | 26.3 |
| Average | 18.4 | 18.5 | 16.0 | 19.9 | 33.0 | 15.4 | 9.3 | 15.1 | 11.5 | 33.9 | 25.3 | 35.8 |

Table 5 reveals that the leucovorin-administered group showed a higher concentration of active folic acid in the plasma than the control group.

The weights of the piglets were also measured at the time of the blood sampling. The results are shown in Table 6.

TABLE 6

| Day | Day 4 | Day 9 | Day 18 | Day 25 |
| --- | --- | --- | --- | --- |
| Leucovorin administered group Average weight (kg) | 2.0 | 3.1 | 4.9 | 7.0 |
| Control group Average weight (kg) | 1.9 | 3.0 | 4.7 | 6.4 |

Table 6 reveals that the leucovorin-administered group showed a higher fattening efficiency than the control group.

In accordance with this invention, the oral administration of a reduced form of (active) folic acid increases the amount of active folic acid in the plasma of fattening pigs and easily improves the fattening efficiency, thereby making it possible to shorten the delivery period or to improve the feed efficiency. Thus, this invention greatly contributes toward the management of the pig-raising industry.

The present application is based on Japanese Patent Application No. 215857/1994, filed on Sep. 9, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for feeding a fattening pig, comprising orally administering a feed additive which comprises a reduced form of folic acid selected from the group consisting of 7,8-dihydrofolic acid, 5,6,7,8-tetrahydrofolic acid, the poly-gamma-glutamic acid derivative of 5,6,7,8-tetrahydrofolic acid, 5-formyl-$H_4$-folic acid, the poly-gamma-glutamic acid derivative of 5-formyl-$H_4$-folic acid, 5,10-methylene-$H_4$-folic acid, the poly-gamma-glutamic acid derivative of 5,10-methylene-$H_4$-folic acid, 5-methyl-$H_4$-folic acid, the poly-gamma-glutamic acid derivative of 5-methyl-$H_4$-folic acid, 10-formyl-$H_4$-folic acid, the poly-gamma-glutamic acid derivative of 10-formyl-$H_4$-folic acid, 5-forimino-$H_4$-folic acid, and the poly-gamma-glutamic acid derivative of 5-formino-$H_4$-folic acid to a fattening pig either directly or via a breast milk.

2. The method of claim 1, wherein said feed additive comprises a liver powder, disrupted cells, or a cell extract of a microorganism.

3. The method of claim 1, wherein said feed additive is administered in an amount sufficient to result in the administration of 0.1 to 100 μg/kg·weight of fattening pig of said reduced form of folic acid.

4. A method for feeding a fattening pig, comprising orally administering to a fattening pig either directly or via a breast milk, a feed, which comprises:

(a) a feed additive comprising a reduced form of folic acid selected from the group consisting of 7,8-dihydrofolic acid, 5,6,7,8,-tetrahydrofolic acid, the poly-gamma-glutamic acid derivative of 5,6,7,8-tetrahydrofolic acid, 5-formyl-$H_4$-folic acid, the poly-gamma-glutamic acid derivative of 5-formyl-$H_4$-folic acid, 5,10-methylene-$H_4$-folic acid, the poly-gamma-glutamic acid derivative of 5,10-methylene-$H_4$-folic acid, 5-methyl-$H_4$-folic acid, the poly-gamma-glutamic acid derivative of 5-methyl-$H_4$-folic acid, 10-formyl-$H_4$ folic acid, the poly-gamma-glutamic acid derivative of 10-formyl-$H_4$-folic acid, 5formino-$H_4$-folic acid, and the poly-gamma-glutamic acid derivative of 5-forimino-$H_4$-folic acid; and (b) a base feed.

5. The method of claim 4, wherein said feed additive comprises a liver powder, disrupted cells, or a cell extract of a microorganism.

6. The method of claim 4, wherein said feed is administered in an amount sufficient to result in the administration of 0.1 to 100 μg/kg·weight of fattening pig of said reduced form of folic acid.

7. The method of claim 4, wherein said base feed comprises at least one element selected from the group consisting of corn, sorghum, barley, wheat, soybean, peanut, canola, fish meal, milk products, fats, oils, vitamins, minerals and mixtures thereof.

* * * * *